(12) United States Patent
Hiriyannaiah et al.

(10) Patent No.: US 9,197,899 B2
(45) Date of Patent: *Nov. 24, 2015

(54) DYNAMIC ADJUSTMENT OF IMAGE COMPRESSION FOR HIGH RESOLUTION LIVE MEDICAL IMAGE SHARING

(71) Applicant: eagleyemed, Inc., Santa Clara, CA (US)

(72) Inventors: Harish P. Hiriyannaiah, San Jose, CA (US); Muhammad Zafar Javed Shahid, San Jose, CA (US)

(73) Assignee: Eagleyemed Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/563,192

(22) Filed: Dec. 8, 2014

(65) Prior Publication Data

US 2015/0092838 A1  Apr. 2, 2015

Related U.S. Application Data

(63) Continuation of application No. 14/291,567, filed on May 30, 2014.

(60) Provisional application No. 61/829,887, filed on May 31, 2013.

(51) Int. Cl.
*H04L 12/28* (2006.01)
*H04N 19/146* (2014.01)
*A61B 8/00* (2006.01)
*H04N 19/172* (2014.01)
*H04N 19/12* (2014.01)
*H04N 19/124* (2014.01)
*H04N 19/132* (2014.01)
*H04N 19/164* (2014.01)
*H04N 19/166* (2014.01)
*H04J 1/16* (2006.01)
*A61B 6/00* (2006.01)

(52) U.S. Cl.
CPC .............. *H04N 19/146* (2014.11); *A61B 8/565* (2013.01); *H04N 19/12* (2014.11); *H04N 19/124* (2014.11); *H04N 19/132* (2014.11); *H04N 19/164* (2014.11); *H04N 19/166* (2014.11); *H04N 19/172* (2014.11); *A61B 6/563* (2013.01)

(58) Field of Classification Search
USPC .......................................... 370/252, 230, 477
See application file for complete search history.

(56) References Cited

U.S. PATENT DOCUMENTS

| | | | |
|---|---|---|---|
| 2004/0015079 A1 | 1/2004 | Berger et al. | |
| 2004/0240543 A1 | 12/2004 | Faroudja | |
| 2005/0013244 A1 | 1/2005 | Parlos | |
| 2008/0037880 A1* | 2/2008 | Lai | 382/232 |
| 2014/0095561 A1* | 4/2014 | Wegener | 708/203 |
| 2014/0357993 A1 | 12/2014 | Hiriyannaiah et al. | |

OTHER PUBLICATIONS

International Search Report dated Nov. 6, 2014 from International Application No. PCT/US 14/40381.
Written Opinion dated Nov. 6, 2014 from International Application No. PCT/US 14/40381.

\* cited by examiner

*Primary Examiner* — John Pezzlo
(74) *Attorney, Agent, or Firm* — Beyer Law Group LLP

(57) ABSTRACT

A video stream of live medical images is generated at a local site having a medical image scanner. A live video stream is transmitted to at least one remote site via a network, which may include wired or wireless Internet connections. Network conditions are monitored during a network session and predictions are made on a predicted bit rate for transmission. The compression parameters for the live video stream are selected based on the predicted bit rate.

30 Claims, 6 Drawing Sheets

DYNAMIC ADJUSTMENT OF IMAGE COMPRESSION FOR HIGH RESOLUTION LIVE MEDICAL IMAGE SHARING

CROSS REFERENCE TO RELATED APPLICATIONS

The present application is a Continuation of U.S. application Ser. No. 14/291,567, filed on May 30, 2014, which claims the benefit of U.S. Provisional Application No. 61/829,887, filed on May 31, 2013, the contents of both are hereby incorporated by reference.

FIELD OF THE INVENTION

The present invention is generally related to techniques for live sharing over the Internet of a video stream composed of high resolution medical images, such as ultrasound images. More particularly, the present invention is directly to dynamically adapting compression techniques for a video stream of medical images to adjust to variable network conditions.

BACKGROUND OF THE INVENTION

In telemedicine applications there is a need to share medical data between different sites. However, one problem in the industry is that some medical imaging applications require a large bandwidth to stream as a live video stream of medical images. Illustrative examples include live video streaming of ultrasound imaging, angiography, and endoscopy. Many types of medical images are difficult to efficiently compress. For example, ultrasound images have a high entropy content and have compression ratios that are dramatically lower than the compression ratios that can be achieved for streaming television and movies. An additional complication is that many small clinics have poor IT infrastructure with marginal and time-varying connections to the Internet, due to cost considerations, remote locations, or other reasons.

As an illustrative example of some of these problems, in ultrasound (u/s) imaging, image frames typically have a resolution of 512×512 pixels that are acquired at frame rates of 10 to 60 frames per second (fps). The frame rate may vary, depending in the u/s frequency of operation. The frame size is usually fixed, and the pixel resolution is again determined by the u/s frequency, and can vary from 400 microns at 2 MHz frequency to 80 microns at 10 MHz frequency. It is this pixel resolution that is relevant to the end-user, not the frame size itself. The frames at the frame rate are usually concatenated to form a standard video stream.

The stated frame size and rates mentioned above imply a raw data rate of 63 Mbps at 30 fps and 8 bits per pixel, gray scale. Without any compression, the data storage required to store one minute of the u/s stream at 30 fps and 8 bits per pixel is 450 MB. For color Doppler u/s imaging 12 bits per pixel is required, implying a raw data rate of about 95 Mbps at 30 fps and a data storage requirement to store one minute of the Doppler u/stream of 675 MB. Consequently, an image compression scheme has to be employed to reduce the bit rate for real-time network transport of the u/s scheme and to reduce the data storage requirements of the u/s scheme. However, the compression requirements for these two use cases need not be identical.

In medical imaging, lossless and lossy compression schemes are employed, depending on the imaging modality. Lossy compression may be employed as long as the quality of compressed images does not violate the Just Noticeable Difference (JND) threshold. This threshold is very subjective, but, many standards bodies such as the American College of Radiology (ACR) have established guidelines for compression rates for various medical imaging modalities.

Ultrasound images have a high entropy content and cannot be compressed with as high a compression ratio as conventional video streams for movies. For ultrasound imaging, many different compression standards are allowed. Examples of permissible compression standards for ultrasound imaging include Motion JPEG2000 (MJPEG2000), MPEG-4 and H.264.

Motion JPEG is a video codec in which each frame is separately compressed into a JPEG image. As a result the quality of the video compression is independent of the motion of the image. At low bandwidth availability priority is given to image resolution. In contrast, MPEG-4 is a standard that sends a reference frame and difference data for following frames (I frames, B frames, and P frames).

In the case of MJPEG2000, each image frame is compressed (either lossy or lossless) and every frame in the 30 fps stream is sent separately. Typical lossy compression rates (compression ratios) are of the order of 1:10 to 1:15. Further effective compression rates are not possible without losing image quality, since inter-frame data redundancy is not captured in MJPEG2000. Thus, while the compression rates of 1:10 to 1:15 rates of MJPEG2000 are good, there are problems in using MGPEG2000 for data storage or for network transport.

In the case of MPEG-4 and H.264, larger compression rates, from 1:20 through 1:80, are possible, since they utilize frame-to-frame redundancies and motion vector compensation schemes. For high entropy content images, such as ultrasound, the compression rates on the order of up to 1:20 to 1:40 are possible. These compression standards also allow for segmenting the images into multiple slices, and apply different compression rates for different schemes. An ultrasound image typically includes a main ultrasound image 105 (the active sub-image taken by the ultrasound probe) and border regions 110, 115 which may include labeling or text describing aspects of the image. Thus an image can often be segmented into strips. For the image example in FIG. 1, the image can be segmented into three strips—a top stripe having some textual data, a left stripe having textual data and the remaining sub-image which corresponds to the ultrasound image data.

The top and left stripes are highly compressible, to a few bytes, since inter-frame redundancies are very high. The active sub-image will have a lower compression rate, based on the mobility of the organ under exam.

Image data may be sent via a wired or wireless network. In a networked environment such as the internet, where these u/s streams are transported in real-time, there are dynamic conditions of the network that can momentarily constrict or disrupt the available bandwidth for u/s stream transport. As a result there can be a severe loss in the quality of the real time transaction and/or a loss in the connection, which is unacceptable in many applications.

SUMMARY OF THE INVENTION

An apparatus, system, method and computer readable medium is disclosed to dynamically adjust compression parameters for a live video stream of medical imaging data in a network having variable network conditions. Quality of Service (QOS) metrics are monitored for a network session between at least two sites. In one embodiment the QOS metrics are used to predict a minimum expected bit rate. The minimum expected bit rate is used to select compression parameters for compressing the live video stream of medical imaging data. The compression parameter may include different video compression protocols and selectable parameters within an individual compression protocol. In one embodiment the quality of service metrics are also used to select a network transmission protocol for transmitting the video stream.

DETAILED DESCRIPTION

Figure 1:
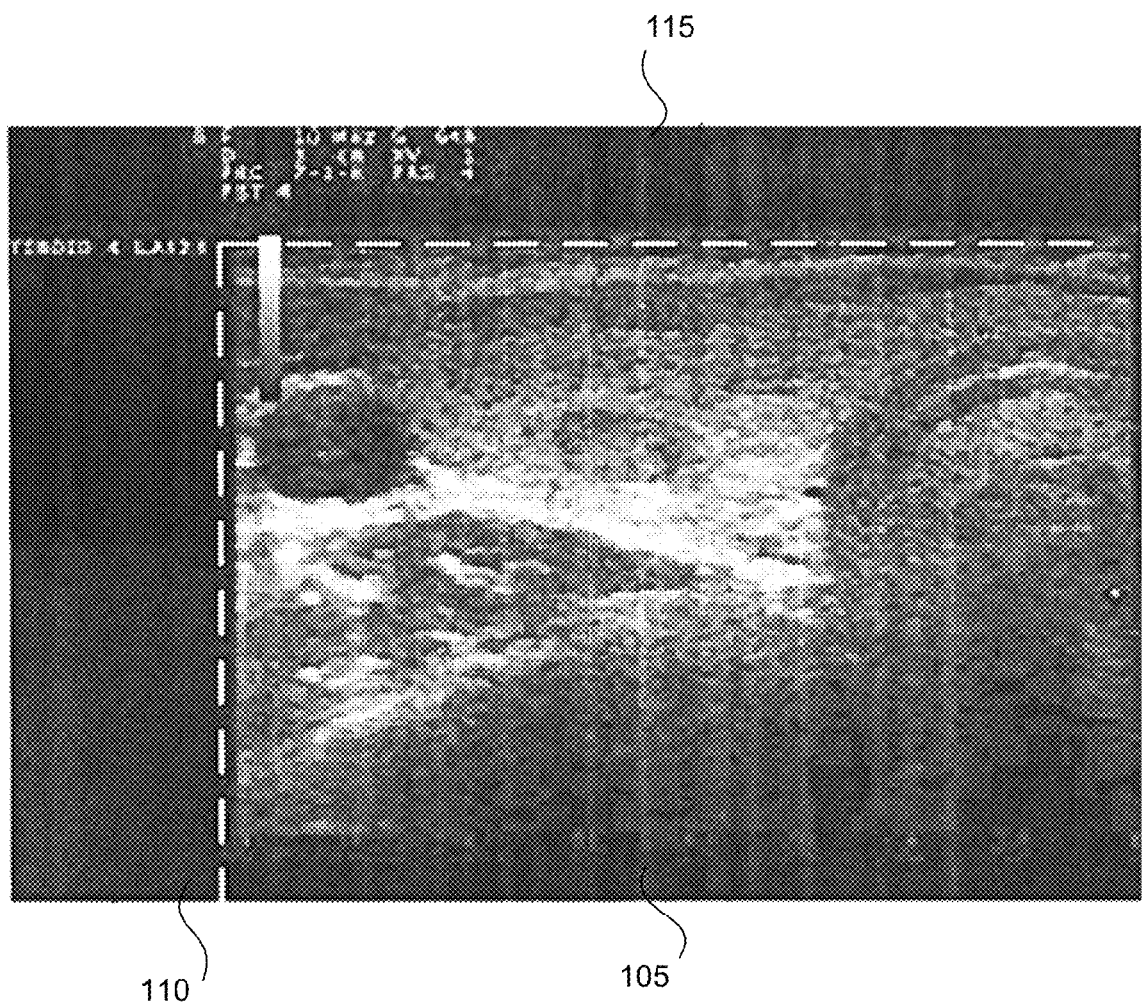
FIG. 1 illustrates a conventional ultrasound image with dashed lines superimposed to illustrate aspects of image compression.
Figure 2:
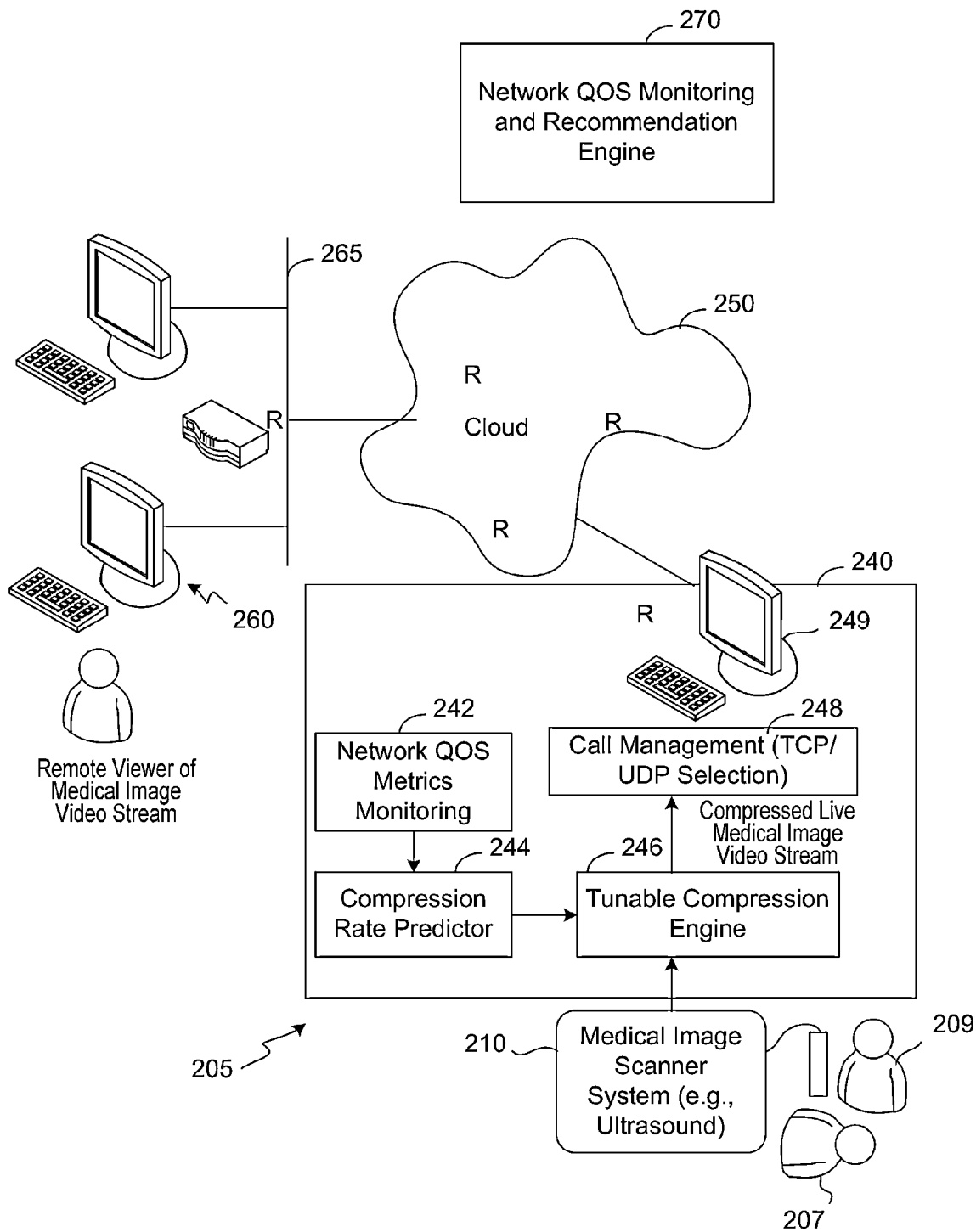
FIG. 2 illustrates a system for dynamically adjusting compression parameters of a video stream of medical imaging data in accordance with an embodiment of the present invention.

FIG. 2 illustrates an exemplary system and network environment for sharing a video stream of compressed medical images. At a local clinic site 205 a patient 207 is examined by a doctor 209 or a medical technician. The patient may be a human patient. Alternatively, many medical imaging procedures have been adapted for veterinary medicine such that the patient may be a cat, dog, horse, etc. A medical imaging scanning device 210 generates a live stream of video images that are transmitted over a network to another site 260, such as local area network 265 of a medical center. As an illustrative example, the live stream may be transmitted to a site of a specialist doctor or a doctor from whom a second opinion is desired. It is also understood that the live stream may also be transmitted simultaneously to other sites.

An exemplary medical imaging scanning device 210 is an ultrasound imaging device, although more generally other types of live imaging device could be used, such as angiography or endoscopy. For the case of ultrasound there is high entropy content of the images in the video stream which in turn invokes many tradeoffs in regards to the compression parameters used to compress the images. Exemplary imaging technologies may require frame rates of 10-60 fps, 8 bits per pixel gray scale and 12 bits for color images, such as color Doppler ultrasound images. In the case of ultrasound imaging, image frames may have a resolution of 512×512 pixels at frame rates of 30 fps and 8 bits per pixel, the raw data rate is 63 Mbps. Other medical imaging techniques, such as angiography, have similar data requirements.

The present invention is generally directed to the use of dynamically adapting a compression scheme used for transporting a medical image video stream, such as an ultrasound stream, across a network with time varying network session connection quality using feedback from at least one network quality of service agent. A live stream of medical images carries a large amount of data. Additionally, certain types of medical data, such as ultrasound images, are difficult to efficiently compress. Moreover, the network connection quality between sites may vary dramatically. For example, a doctor at a small clinic may have a poor quality connection to the Internet. As a result of these factors, compressing the live video stream of the medical imaging data is performed to attempt to maintain a live connection with minimal degradation of the quality of the live images.

The network path to a remote viewer at site 260 includes the Internet network cloud 250 and any local networks, such as local network 265. Reporting (R) tools are network agents that provide network metrics at different part of the network communication path. Typically there would be reporting tools configured in at least both ends of the network path. These network metrics may include attributes such as bandwidth, packet loss, and packet corruption. The reporting tools may comprise commercial or proprietary reporting tools. The frequency with which reports are received may be configured. For example, many commercial network reporting tools permit periodic generation of reports on network conditions such as once every 100 ms, once every second, once every five seconds, etc.

The network quality of service (QOS) metrics are monitored and used to predict network conditions (in the near future) to determine optimum compression parameters for transmitting a live video stream of medical images to the remote viewer. That is, the QOS metrics provide metrics on past and recent network conditions, which are then used to predict network conditions when a frame of the live video stream is transmitted. For example, suppose the reporting tools provide a report every 5 seconds. In this example, if the last report was received 3 seconds ago, data on the past and most recent report (3 seconds ago) on network conditions may be used to predict network conditions to transmit a video frame. In particular, an expected minimum bit rate may be calculated based on quality of service inputs such as predicted bandwidth, predicted packet loss, and predicted packet latency. This minimum bit rate of the connection session, in turn, implies a compression rate, or compression ratio, for the live stream of medical images.

Block 240 illustrates an example of modules to dynamically adjust compression parameters as network conditions vary. In one embodiment a local computer 249 includes software modules to perform network QOS monitoring 242, compression rate prediction 244, a tunable compression engine 246, and a call management selection module 248. In one embodiment the call management selection module 248 also receives the QOS metrics from network QOS monitoring module 242 and selects the network transmission protocol (e.g., TCP or UDP) based on the network conditions.

The tunable compression engine 244 has compression parameters that are selectable. The selectable parameters may include different compression protocols and/or selectable features within one protocol. The tunable compression engine selects the compression technique, based on the predicted compression rate, to optimize the image quality for the medical images of the live video stream. In particular, the tunable compression engine may select the compression technique to minimize distortion of the video images given the constraint of the predicted bit rate and that certain types of medical images, such as ultrasound images, have a high entropy content. The compressed live medical image stream is transmitted using a network protocol, which may also be adjusted based on network conditions.

Figure 3:
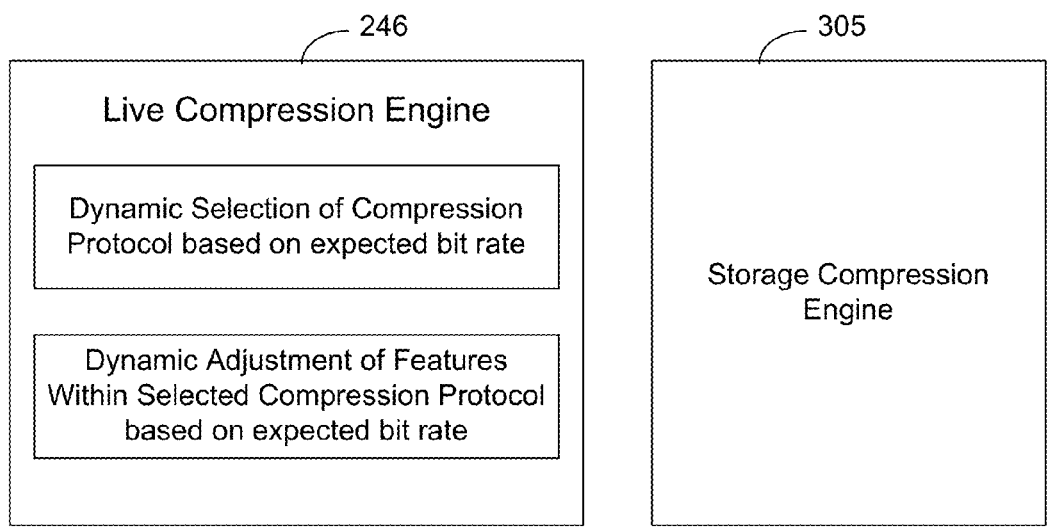
FIG. 3 illustrates a tunable compression engine in accordance with an embodiment of the present invention.

FIG. 3 is a functional block diagram illustrating additional aspects of the compression engine 246. A rule-based system may select an optimum compression technique to transmit a live video stream of medical images with minimal distortion. That is, certain ranges of parameters, such as bandwidth, loss, and packet corruption, are mapped to specific compression parameters. The compression engine in one embodiment selects a compression protocol from a choice of at least two different compression protocols used in transmitting live video streams of medical images. The compression engine may also make dynamic adjustments to individual selectable features of an individual compression protocol. The compression engine is a flexible engine. Depending on the available bandwidth (predicted bit rate), it can switch dynamically between different video compression protocols. In one embodiment it can dynamically switch between MJPEG2000 compression and standard MPEG-4/H.264 schemes. More generally, it is contemplated that other currently implemented and proposed compression standards may be selected. Other examples of video compression protocol standards that may be selected include H.265, VP8, and VP9. Additionally, in one embodiment at least one compression protocol has selectable features that can be turned on or off. In the case of MPEG-4 and H.264, compression rates are adjusted by one or more of:

1) turning on or off MVC encoding,
2) varying the block sizes of frames,
3) varying the quantization tables for intra-frame discrete cosine transform (DCT) compression,
4) varying motion vector compensation (MVC) for inter-frame compression, and
5) reducing the stream frame rate by dropping frames ahead of the compression engine.

As also illustrated in FIG. 3, in one embodiment an additional storage compression engine 305 may be provided to optimize compression for storage. In some applications it may be desirable to also store the video stream. Consequently, as illustrated in FIG. 3, a parallel compression engine for storage of the compressed medical image video stream may be provided that is not subject to such dynamic compression schemes. The compression engine for storage may use a constant conservative compression rate applied to the stream that will not compromise the JND threshold guidelines of the ACR.

Note that the compression engine can adapt rapidly to changing network conditions. In many parts of the world doctor's offices and small clinics may use wireless local networks and/or wireless Internet connections. However, the quality of these connections may depend on the time of day and other factors. For example, a clinic close to a train track may experience large changes in the quality of a wireless Internet connection whenever a train travels close to the clinic, due to the reflection from the metal surface of the train. As another example, for the case of a small clinic using a WiFi connection, the quality of WiFi service may vary based on time of day and number of users. Wireless internet connections based on the 802.11 standard may suffer interference and packet drop at times of the day when there are many users on individual wireless networks and on neighboring wireless networks. As an example, many wireless internet systems in individual portions of a city slow down between the hours of 5 PM to 8 PM as multiple users in the same geographic region attempt to simultaneously access the Internet.

The compression engine 246 compresses the video stream prior to transmission. In practice the network has time-varying quality of service (QOS) characteristics, such as packet loss, bandwidth, and packet corruption. If fixed (non-varying) compression techniques are used then in the worst case the changing network conditions can result in a severe loss in the quality of the real time transaction and a possible loss in connection, which is unacceptable. In accordance with an embodiment of the present invention, the compression engine reacts to such changing conditions by monitoring network conditions and adapting the compression technique used to compress the video stream. The compression scheme is adapted to the dynamic conditions of the network by utilizing a variable rate compression scheme. For the data archival use-case, a fixed rate compression scheme is adequate and the rate is based on the JND metric for the specimen being imaged.

Figure 4:
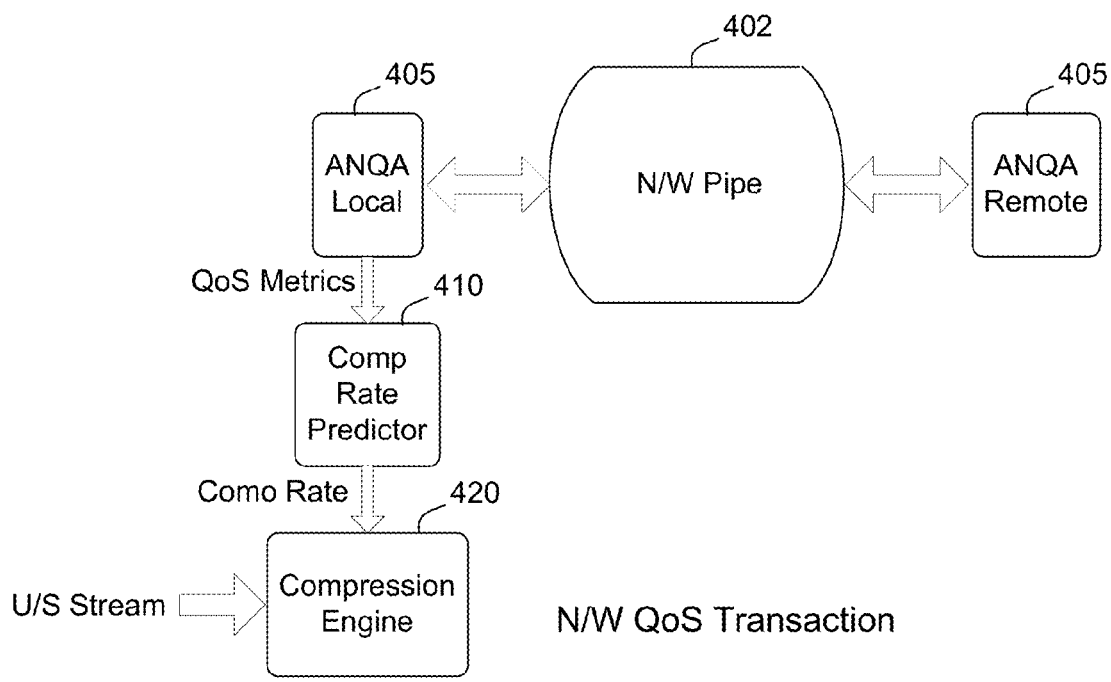
FIG. 4 illustrates aspects of a network QOS transaction in accordance with an embodiment of the present invention.

FIG. 4 illustrates aspects related to the use of Active Network Quality Agents (ANQA) for an ultrasound (u/s) embodiment. The ANQA elements 405 serve as the reporting (R) agents. In a network session the network can be pictured as a network pipe 402 between local and remote sites. The ANQA elements may be based on proprietary software or on commercial solutions. As an example, commercial products, such as the Airwave software of Aruba Networks, Inc., provide network Quality of Service (QOS) metrics, and can be configured to report these statistics to desired locations. The ANQA elements may be local and remote reporting elements, although more generally there may be additional ANQA elements at different points in the network. Examples of QOS metrics include current bandwidth (BW) for TCP connections and packet loss rate (PLR) for UDP connections In one embodiment, the Active Network Quality Agent (ANQA) continually monitors the available QOS metrics for a network session. In one embodiment a prediction scheme for determining the available bandwidth is utilized. That, is the current and recent reporting results from the ANQA agents are used to predict the expected bit rate along the transmission path when the video is transmitted.

The ANQA reporting agent(s) 405 report the QoS metrics to the Compression Rate Predictor (CRP) 410, which outputs a compression rate to the compression engine 420. The CRP may rely on available metrics for current and immediate past of network Quality of Service (QoS) to predict a compression rate which would be compatible with the network conditions.

The CRP may, for example, utilize linear or non-linear prediction techniques for compression rate prediction. That is, a variety of different well-known prediction algorithms may be modified to take the QOS metrics (e.g., bandwidth, packet loss, and packet corruption) and generate an expected bit rate for the compression engine.

Figure 5:
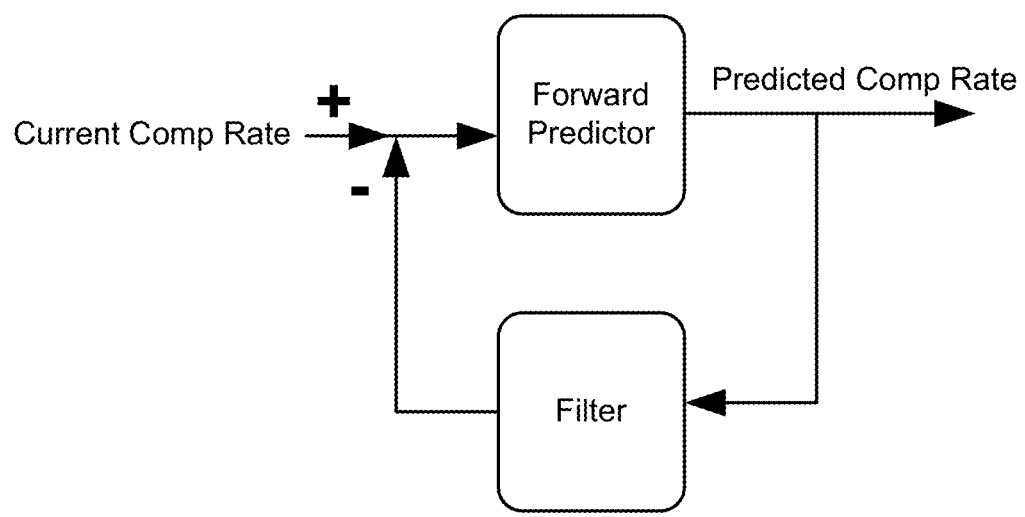
FIG. 5 illustrates prediction of compression rate in accordance with an embodiment of the present invention.

A variety of linear prediction algorithms may, for example, predict network quality (e.g., packet loss, bandwidth) based on regression techniques and, curve fitting based on the measured QOS metrics to predict network characteristics. Referring to FIG. 5, in one embodiment, a filter is provided in combination with a forward predictor. The current compression rate is an input and the output is a predicated compression rate. In one embodiment a Linear Prediction algorithm utilizes Auto-Regressive Moving-Average (ARMA) models that utilize an error correction scheme such that the filter would be an ARMA filter. Kalman Prediction (KP) may also be used by the compression rate predictor. As examples, any KP scheme (Linear or Non-Linear) that is modeled in a higher order state space scheme may be used. Additionally, Hidden Markov Model (HMM) Prediction may be used by the compression rate predictor.

In one embodiment the monitoring rate of ANQA agents is adjustable. For example, this monitoring can be done every second to about few times a minute. This monitoring rate can also be subject to a prediction scheme, based on the rate of change of QoS, in a manner similar to the compression rate prediction.

Figure 6:
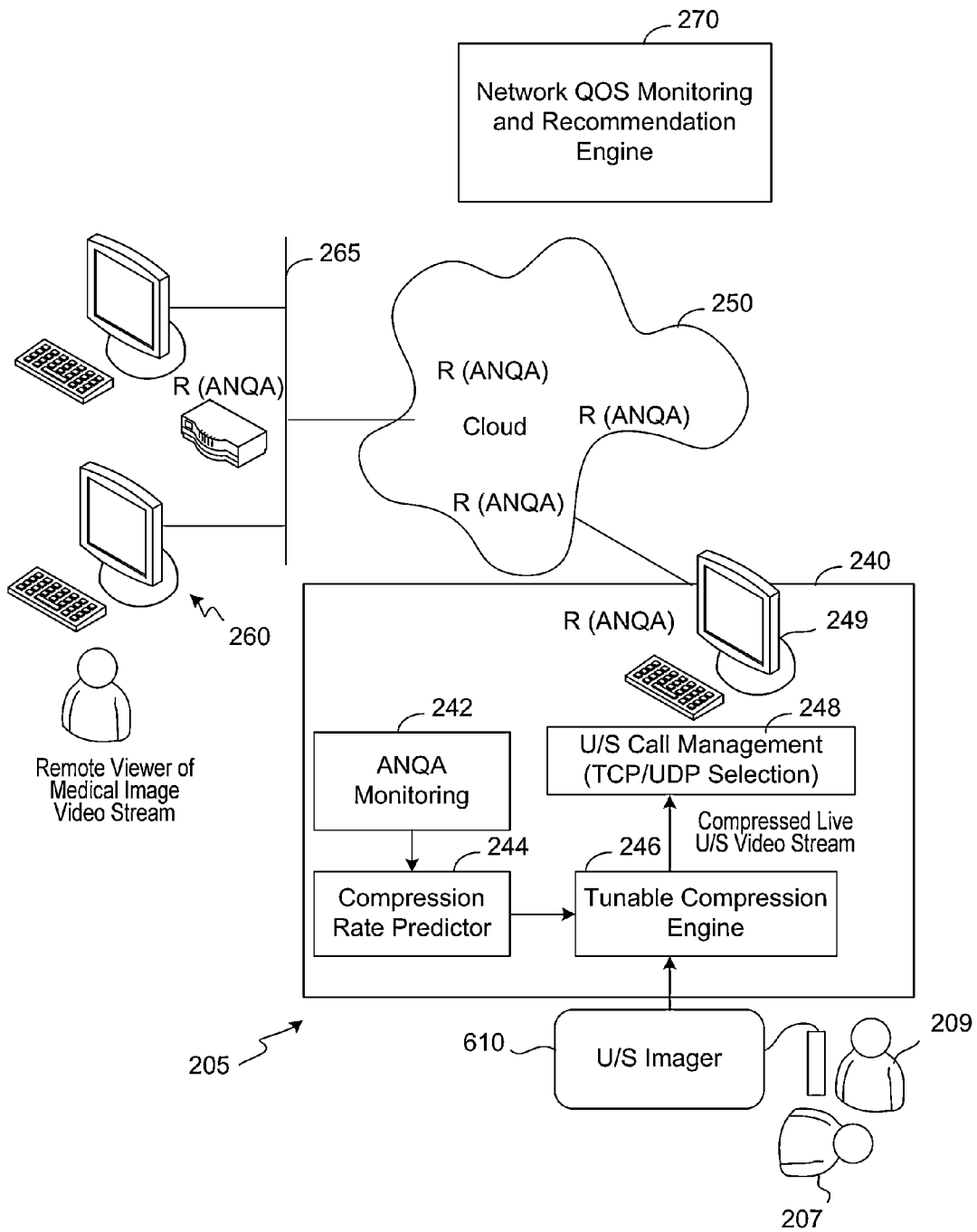
FIG. 6 illustrates selection of network transmission protocol based on network conditions in accordance with an embodiment of the present invention.

FIG. 6 illustrates an example for the medical image scanner being an ultrasound imager 610. Referring to FIG. 6, in one embodiment the ANQA are used to support a call management system dynamically switching between different network transmission protocols (e.g., Transmission Control Protocol (TCP) and User Datagram Protocol (UDP) protocols) based on QoS metrics. To monitor an individual session, at least one ANQA agent is monitored, Preferably at least two ANQA agents (one at either end of the network connection is monitored). Additional ANQA agents in the cloud may also be optionally monitored. There are tradeoffs, in terms of bandwidth and packet loss for different network protocols. TCP, for example, provides for retransmission of dropped packets and thus requires higher bandwidth than UDP. UDP has lower bandwidth and lower latency requirements but does not guarantee delivery of packets.

Additionally, as previously discussed, the QOS metrics may different slightly for TCP vs. UDP and thus have to be factored into the compression rate predictor. Thus, the network transmission protocol may be selected to optimize the quality of the live video stream in view of the QOS metrics. While TCP and UDP are examples of network transmission protocols, it will be noted that other network transmission protocols are contemplated, such as Stream Control Transmission Protocol (SCTP).

In one embodiment the QOS statistics during use of the medical image scanner may also be monitored by a service entity to provide recommendations. The QOS statistics provide information on the network connection quality. The QOS statistics may also be collected over many different sessions. As a result, temporal patterns may be detected. A large hospital or clinic may have a dedicated in-house information technology capability. However, small clinics or individual doctor soften lack such capabilities and under-invest in information technology services. In one embodiment a rule based system may provide recommendations on how an upgrade in network capabilities (e.g. connection type and/or connection bandwidth) may improve performance.

It will be understood that the networks metrics monitoring, compression rate predictor, tunable compression engine, and call management may be implemented in different ways. In one embodiment they are implemented as software modules operating on a local computer. Alternatively, it will be understood that some or all of the modules may be implemented within a medical image scanner. It will be understood that the software modules and methodologies may be stored as computer readable instructions stored on a non-transitory computer readable medium.

While the invention has been described in conjunction with specific embodiments, it will be understood that it is not intended to limit the invention to the described embodiments. On the contrary, it is intended to cover alternatives, modifications, and equivalents as may be included within the spirit and scope of the invention as defined by the appended claims. The present invention may be practiced without some or all of these specific details. In addition, well known features may not have been described in detail to avoid unnecessarily obscuring the invention. In accordance with the present invention, the components, process steps, and/or data structures may be implemented using various types of operating systems, programming languages, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein. The present invention may also be tangibly embodied as a set of computer instructions stored on a computer readable medium, such as a memory device.

What is claimed is:

1. A method of sharing medical information that includes streaming of ultrasound imaging data, comprising:
   receiving, at a computing device, a live ultrasound video stream generated by an ultrasound medical imaging scanner at a first medical site;
   monitoring, at the computing device, a set of quality of service metrics for a network communication session between the first medical site and a second medical site;
   predicting, based on the set of quality of service metrics, a minimum expected bit rate to transmit a live video stream from the first medical site to the second medical site that includes a compressed version of the live ultrasound video stream;
   selecting, in response to the minimum expected bit rate, video compression parameters to compress the live ultrasound video stream selected to maintain a live video stream based on the minimum expected bit rate;
   compressing, at the computing device, the live ultrasound video stream according to the selected video compression parameters; and
   transmitting the compressed live ultrasound video stream from the first medical site to the second medical site.

2. The method of claim 1, wherein the predicting and the selecting is performed by a compression rate predictor and the compressing is performed by a tunable compression engine.

3. The method of claim 1, wherein the at least one quality of service metric comprises a bandwidth metric, a packet loss metric, a packet latency, and a packet corruption metric.

4. The method of claim 1, wherein the predicting comprises a prediction technique selected from the group consisting of a linear predication algorithm and a nonlinear prediction algorithm.

5. The method of claim 1, wherein the predicting comprises a prediction technique selected from the group consisting of a linear prediction algorithm, Kalman prediction, and hidden Markov model prediction.

6. The method of claim 1, wherein the predicting comprises predicting the minimum expected bit rate from past data on quality of service metrics for a time when a frame will be transmitted.

7. The method of claim 1, wherein the selecting comprises selecting from at least two different video compression protocols.

8. The method of claim 7, wherein the at least two different video compression protocols include a MJPEG2000 compression protocol and at least one of MPEG-4, H.264, H.265, VP8, and VP9.

9. The method of claim 1, wherein the selecting comprises selecting a subset of features of a particular video compression protocol.

10. The method of claim 9, wherein the selecting a subset of features includes selecting at least one of:
    varying the block sizes of frames;
    varying the quantization tables for intra-frame discrete cosine transform (DCT) compression;
    varying motion vector compensation (MVC) for inter-frame compression;
    turning on or off the MVC encoding; and
    reducing the stream frame rate by dropping frames ahead of the compression engine.

11. The method of claim 1, further comprising selecting a transmission protocol based on the expected bit rate.

12. The method of claim 1, further comprising analyzing quality of service metrics for a plurality of sessions and providing a network service recommendation.

13. A method of tuning video compression parameters for a live video stream of medical images in a networked telemedicine environment having variable network quality, comprising:
- receiving, at a computing device, feedback on network conditions for a network session between a first medical site having an ultrasound medical imaging scanner and a second medical site; and
- dynamically adapting a compression scheme, at the computing device, used to transport a live medical image video stream of ultrasound images from the first medical site to the second medical site based on the received feedback on network conditions for the network session, including:
  - predicting, based on the feedback on network conditions, a minimum expected bit rate to transmit a compressed live video stream of high resolution medical images from the medical imaging scanner from the first medical site to the second medical site;
  - selecting, in response to the expected bit rate, video compression parameters for the live medical image video stream of ultrasound images; and
  - compressing the live medical image video stream of ultrasound images, using the selected video compression parameters.

14. The method of claim 13, wherein the feedback includes monitoring at least one quality of service metric.

15. The method of claim 14, wherein the at least one quality of service metric comprises a bandwidth metric, a packet loss metric, a packet latency, and a packet corruption metric.

16. The method of claim 14, further comprising analyzing quality of service metrics for a plurality of sessions and providing a network service recommendation.

17. The method of claim 13, wherein the predicting comprises a prediction technique selected from the group consisting of a linear predication algorithm and a nonlinear prediction algorithm.

18. The method of claim 13, wherein the predicting comprises a prediction technique selected from the group consisting of a set of linear prediction algorithms, Kalman prediction, and hidden Markov model prediction.

19. The method of claim 13, wherein the selecting comprises selecting from at least two different video compression protocols.

20. The method of claim 19, wherein the at least two different video compression protocols include a MJPEG2000 compression protocol and at least one of MPEG-4, H.264, H.265, VP8, and VP9.

21. The method of claim 13, wherein the selecting comprises selecting a subset of features of a particular video compression protocol.

22. The method of claim 21, wherein the selecting a subset of features includes selecting at least one of:
- varying the block sizes of frames;
- varying the quantization tables for intra-frame discrete cosine transform (DCT) compression;
- varying motion vector compensation (MVC) for inter-frame compression;
- turning on or off the MVC encoding; and
- reducing the stream frame rate by dropping frames ahead of the compression engine.

23. The method of claim 22, further comprising selecting a transmission protocol based on the expected bit rate.

24. A non-transitory computer readable medium having computer code instruction which when executed on a computer process implements a method comprising:
- receiving feedback on network conditions for a network session between a first medical site having an ultrasound medical imaging scanner and a second medical site; and
- dynamically adapting a compression scheme used to transport a live medical image video stream of ultrasound images from the first medical site to the second medical site based on the received feedback on network conditions for the network session, including:
  - predicting, based on the feedback on network conditions, a minimum expected bit rate to transmit a compressed live video stream of high resolution medical images from the medical imaging scanner from the first medical site to the second medical site;
  - selecting, in response to the expected bit rate, video compression parameters for the live medical image video stream of ultrasound images; and
  - compressing the live medical image video stream of ultrasound images, using the selected video compression parameters.

25. The non-transitory computer readable medium of claim 24, wherein the predicting comprises a prediction technique selected from the group consisting of a linear predication algorithm and a nonlinear prediction algorithm.

26. The non-transitory computer readable medium of claim 24, wherein the predicting comprises a prediction technique selected from the group consisting of a set of linear prediction algorithms, Kalman prediction, and hidden Markov model prediction.

27. The non-transitory computer readable medium of claim 24, wherein the selecting comprises selecting from at least two different video compression protocols.

28. The non-transitory computer readable medium of claim 24, wherein the selecting comprises selecting a subset of features of a particular video compression protocol.

29. The non-transitory computer readable medium of claim 28, wherein the selecting a subset of features includes selecting at least one of:
- varying the block sizes of frames;
- varying the quantization tables for intra-frame discrete cosine transform (DCT) compression;
- varying motion vector compensation (MVC) for inter-frame compression;
- turning on or off the MVC encoding; and
- reducing the stream frame rate by dropping frames ahead of the compression engine.

30. A method of tuning video compression parameters for a live video stream of medical images in a networked telemedicine environment having variable network quality, comprising:
- receiving, at a computing device, feedback on network conditions for a network session between a first medical site having an ultrasound medical imaging scanner and a second medical site, wherein the feedback includes monitoring at least one quality of service metric; and
- dynamically adapting a compression scheme, at the computing device, used to transport a live medical image video stream of ultrasound images from the first medical site to the second medical site based on the received feedback on network conditions for the network session, including:
  - predicting, based on the feedback on network conditions, a minimum expected bit rate to transmit a compressed live video stream of high resolution medical images from the medical imaging scanner from the first medical site to the second medical site;
  - selecting, in response to the expected bit rate, video compression parameters for the live medical image video stream of ultrasound images including selecting from at least two different video compression protocols and further selecting a subset of features in the selected at least one of the two video compression protocols; and compressing the live medical image video stream of ultrasound images, using the selected video compression parameters.

* * * * *